United States Patent [19]

Mueller

[11] 4,094,775

[45] June 13, 1978

[54] DIALYSIS SYSTEM

[75] Inventor: William A. Mueller, Glendale, Calif.

[73] Assignee: California Institute of Technology, Pasadena, Calif.

[21] Appl. No.: 772,434

[22] Filed: Feb. 28, 1977

[51] Int. Cl.² .............................................. B01D 13/00
[52] U.S. Cl. ...................................... 210/22; 210/321 B
[58] Field of Search ......................... 210/22, 23, 321 B

[56] References Cited

U.S. PATENT DOCUMENTS

| | | | |
|---|---|---|---|
| 3,608,729 | 9/1971 | Haselden | 210/321 |
| 3,617,545 | 11/1971 | Dubois | 210/22 |
| 3,669,880 | 6/1972 | Marantz et al. | 210/22 |
| 3,703,959 | 11/1972 | Raymond | 210/321 |

| | | | |
|---|---|---|---|
| 3,994,799 | 11/1976 | Yao et al. | 210/321 A |

Primary Examiner—Charles N. Hart
Assistant Examiner—E. Rollins Cross
Attorney, Agent, or Firm—Marvin E. Jacobs

[57] ABSTRACT

The improved hemodialysis system utilizes a second polymeric membrane having dialyzate in contact with one surface and a urea decomposition solution in contact with the other surface. The membrane selectively passes urea from the dialyzate into the decomposition solution, while preventing passage of positively charged metal ions from the dialyzate into the solution and ammonium ions from the solution into the dialyzate.

19 Claims, 4 Drawing Figures

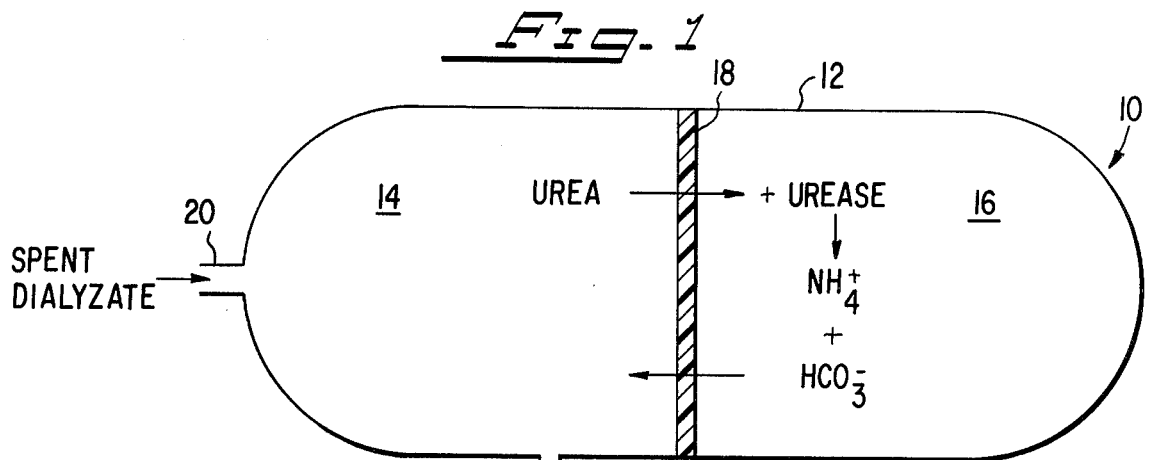
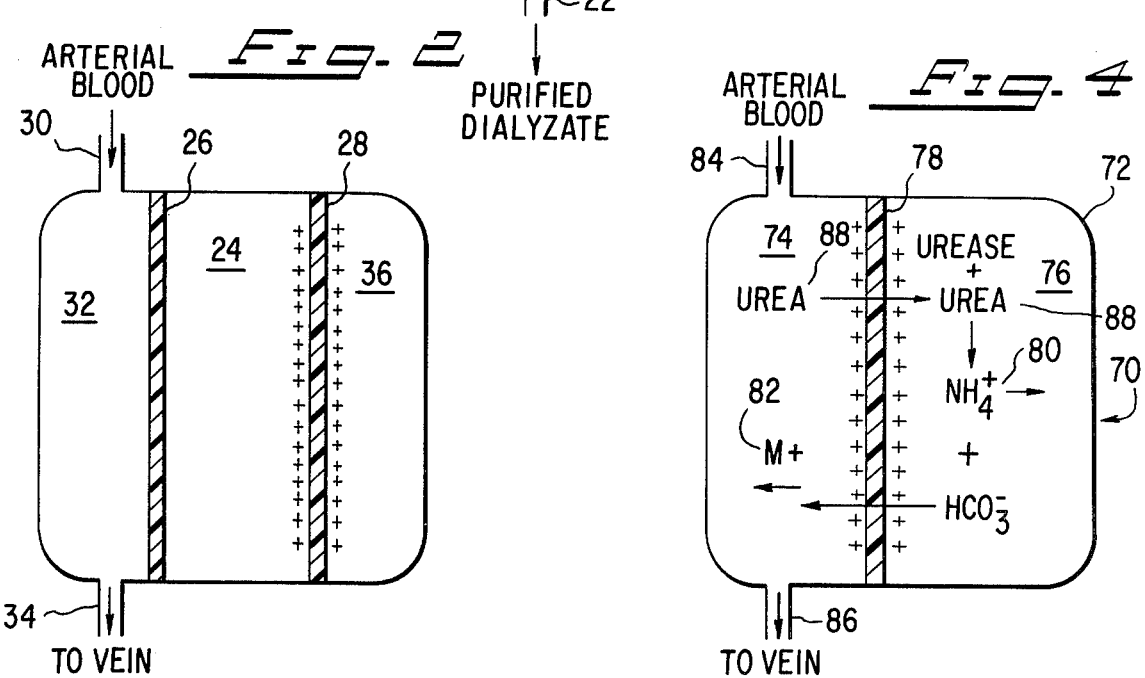
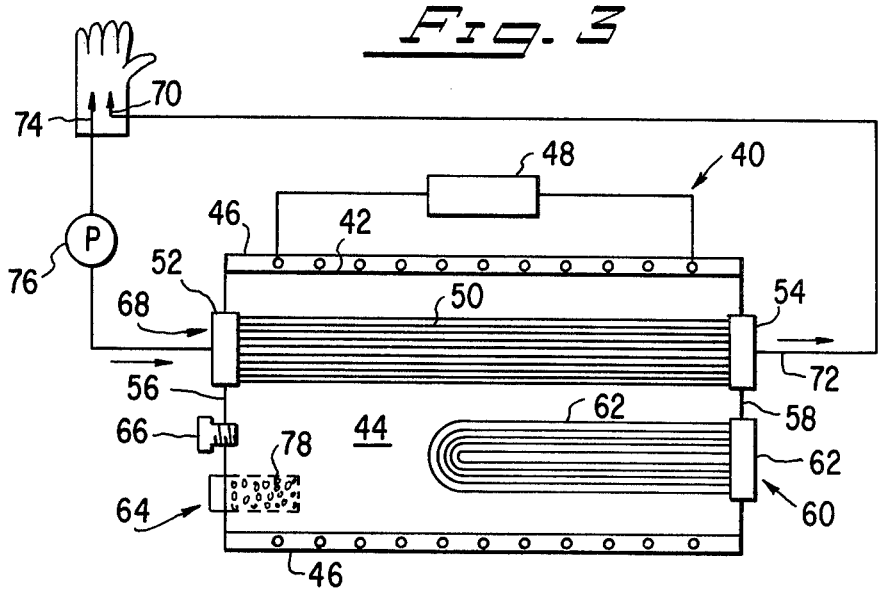

DIALYSIS SYSTEM

ORIGIN OF THE INVENTION

The invention described herein was made in the performance of work under a NASA contract and is subject to the provisions of Section 305 of the National Aeronautics and Space Act of 1958, Public Law 83-568 (72 Stat. 435; 42 USC 2457).

BACKGROUND OF THE INVENTION

1. Field of the Invention

The present invention relates to a hemodialysis system and, more particularly, to an improved system for selectively removing urea from dialyzate.

2. Description of the Prior Art

A sizable fraction of the estimated 50,000 people who die of kidney failure each year in the United States are free of other complications and might be restored to useful life if their kidney function could be provided artificially. At present, artificial kidneys (using hemodialysis) and clinical procedures have been developed to the point where long-term sustenance of life by periodic hemodialysis is practical in many cases.

The limitations in using hemodialysis are the small number of patients who can be treated with a given kidney machine and the considerable expense of maintaining and staffing a kidney-treatment center. Obviously, a desirable solution lies in the development of an artificial kidney which is inexpensive, portable and capable of being operated outside the confines of a hospital with a minimum of medical attention. Attainment of this solution will require increased efficiency of mass transfer and further optimization in design of artificial-kidney systems.

In recent years, considerable attention has been focused on methods of reducing the size of the artificial kidney. This requires miniaturization of the membrane-containing dialyzer and a significant reduction in the volume of dialyzing fluid. It is generally conceded that the toxin primarily responsible for the uremic syndrome has not yet been identified. Even though urea is not considered particularly toxic, its removal is one of the chief objectives of dialysis as practiced today. The reason for the concentration on urea removal is that, in the absence of more specific knowledge, dialysis based on this principle is obviously beneficial. At least two explanations suggest themselves: (a) Unidentified toxicants are removed along with the urea. (b) Urea produces toxic products.

In order to increase the efficiency of hemodialysis, it is desirable to maintain the trans-membrane concentration gradient of waste metabolites as high as possible. Low waste concentrations in the dialyzing fluid have in the past been maintained by two methods. The more widely used method is the continual dilution of the dialyzed substances in a large reservoir of fluid, usually 100 to 300 liters. A second method of maintaining the gradient is to use the dialyzing fluid in a single-pass operation, where the waste-bearing effluent is discarded. Even then, more than 100 liters of fluid are required. The current research trend in obtaining low concentrations of wastes is to remove them selectively from the dialyzing fluid. Such an approach would allow the use of much smaller volumes of dialyzing fluid. Among all waste products, urea is by far the major waste metabolite which must be removed daily from the body fluid. Three major methods of urea removal from dialysate have been reported.

The first procedure utilizes an activated carbon bed which removes urea by absorption. However, the demonstrated capacity for urea is only 0.2–0.8 grams per 100 grams of carbon. In another method urea is reduced by enzymatic hydrolysis either inside microcapsules or by the combination with other absorbents. However, enzymatic decomposition of urea produces large concentrations of ammonium ion which is toxic. Therefore, it is essential to achieve rapidly removal of the ammonium ion or it can accumulate in the dialyzate and enter the blood. A commercial apparatus utilizes sodium zirconium phosphate to remove the ammonia produced by enzymatic decomposition of urea in the presence of urease. Though this system does remove urea from dialyzate it also removes essential metal ions such as strontium and calcium which must be replaced. Furthermore, large amounts of zirconium phosphate are required and the process is expensive since the spent zirconium phosphate absorbent is not regeneratable and must be discarded.

SUMMARY OF THE INVENTION

The improved hemodialysis system in accordance with the invention obviates the need for an ammonia absorbent in the urea decomposition solution. The system of the invention permits purification and recirculation of dialyzate fluid in an efficient manner and substantially reduces the quantity of dialyzate needed for dialysis making it feasible to produce a portable, or wearable artificial kidney system. The degradation products produced by the dialyzate treating portion of the apparatus forms a soluble toxic component and a soluble nontoxic component. The toxic component is retained in the treating section of the apparatus while the nontoxic component may migrate or diffuse back into the dialyzate for safe elimination in the body of the patient. The system of the invention also prevents diffusion of essential metal ions from dialyzate into the treating solution.

Urea is continuously removed from dialyzate in accordance with the invention by passing the urea in contact with a polymeric membrane selectively permeable to urea. The urea passes through the membrane into a solution containing a urea decomposition agent such as the enzyme urease. The urea is decomposed into ammonium and bicarbonate ions. The membrane is selectively impermeable to ammonium ion but may pass the bicarbonate back into dialyzate and eventually through the primary membrane into the blood. However, bicarbonate is nontoxic and is readily decomposed and eliminated by exhalation as carbon dioxide. The membrane used in the dialyzate purification section is also selectively nonpermeable to essential positive cations such as strontium and calcium which remain in the dialyzate obviating the need to replenish these metals as is practiced in commercial systems. Preferred membranes are positively charged membranes, suitably polyquaternary substituted cation exchange resins, since such membranes do not require gradient effects for providing the desired nonselectivity to passage of cations in either direction.

The dialyzate treating apparatus of the invention has demonstrated the capability of removing almost half the urea content of test dialyzates in 20 hours while retaining up to about 90% ammonium ions in the treating chamber. Operation is continuous and regeneration simply involves replacing the low cost urease enzyme. The system substantially reduces the amount of dialyzate required and a small size is indicated for use in current clinical dialyzers in a typical thrice weekly dialysis regimen.

These and many other features and attendant advantages of the invention will become apparent as the invention becomes better understood by reference to the following detailed description when considered in conjunction with the accompanying drawings.

BRIEF DESCRIPTION OF THE DRAWINGS

FIG. 1 is a schematic illustration of a spent dialyzate urea removal unit in accordance with the invention;

FIG. 2 is a schematic illustration of an artificial kidney hemodialysis unit incorporating the dialyzate treating unit of the invention;

FIG. 3 is a schematic illustration of a hollow fiber hemodialysis apparatus in accordance with the invention; and FIG. 4 is a schematic illustration of an artificial kidney machine incorporating a single cationic membrane and having the urease present in the dialyzate.

DESCRIPTION OF THE PREFERRED EMBODIMENTS

Referring now to FIG. 1 the dialyzate treating unit 10 of the invention includes a container 12 divided into a dialyzate chamber 14 and a urea decomposition chamber 16 by a common membrane 18. Spent dialyzate enters chamber 14 through inlet 20 and purified dialyzate leaves through outlet 22. The membrane 18 is permeable to the urea which diffuses into chamber 16 which contains a solution of urease enzyme. The enzyme decomposes the urea into ammonium ion which is repelled by the membrane 18 and is retained in chamber 14 and into bicarbonate which may permeate through the membrane 18 into the dialyzate. The purified dialyzate may be recycled to the dialysis section of a hemodialysis unit.

The membrane 18 is formed of a high molecular weight synthetic polymer having good tensile strength, elongation and flexural strength. The membrane is selectively permeable to solvated urea molecules while preventing passage of larger molecules and preventing passage of cationic ammonium or metallic ions in either direction. Preferred membrane materials are synthetic polymers containing cationic groups such as phosphonium, sulfonium or quaternary nitrogen. A suitable membrane material is RAI P-4025 which is a polyethylene containing 45% grafted vinylpyridine having an ion-exchange capacity of 5 meq/gm and a resistance of 1 ohm-cm$^2$. The membrane may be utilized in various thicknesses depending on the desired flow rate and mechanical properties required in the purification unit. The thickness may be from 1–15 mil, generally around 2–10 mil in thickness. The surface area membrane is selected so as to give adequate removal of urea from the dialyzate. From experiments to date, it is estimated that the surface required would be about 10 to 40 square inches.

The treating chamber 16 should contain concentrations of low molecular weight ingredients equal to that contained in the dialyzate chamber 14. For example, buffer concentration should be equivalent as should saline concentration to prevent diffusion from dialyzate into the treating solution. The urease concentration should be sufficient to significantly decrease the amount of urea in the dialyzate. Usually the urea concentration should be at least 25–300% the concentration of the urea in the dialyzate in order to provide adequate periods before the need to recharge urease to the treating chamber.

The dialyzate treating unit of the invention can be combined with many diverse types of hemodialysis units. In its simplest form shown in FIG. 2 the dialyzate chamber 24 would have one wall formed by the primary membrane 26 and another wall portion formed of the secondary treating membrane 28. Blood from an artery enters the inlet 30 to continuous flow through chamber 32 and leaves through outlet 34. As the blood flows past primary membrane 26 such as a cellulose ester, preferably a cupprammonium treated cellulose acetate, urea diffuses through membrane 26 into the dialyzate chamber 24. The urea in turn will diffuse through secondary positively charged membrane 28 into the treating section 36 where it will be decomposed by urease into ammonium and bicarbonate ions. The bicarbonate ions will build up in concentration and can flow backwards through membrane 28 into the dialyzate and in turn through membrane 26 into the blood. The blood will leave through outlet 34 and will be returned to a vein of the subject by intravenous injection.

In the typical artificial kidney machine a very thin film of flowing blood is separated from the surrounding dialyzate solution by an approximately 3 mil thick semipermeable cellulose acetate membrane. This membrane allows substances in normal molecular solution and the solvent to pass through its pores but it prevents the passage of very large molecules such as proteins and cellular constituents of the blood. The membrane does not permit the passage of bacteria and viruses so that sterilization of the apparatus located outside the membrane is not required. Since the apparatus operates by diffusion and osmosis the dialyzate liquid must contain physiological concentrations of all membrane-passing, dissolved normal constituents of the blood, electrolytes in particular, which are required to be maintained in the blood. The dialyzate may also contain high concentrations of substances which it is desired to introduce into the blood stream by diffusion such as drugs, dextrose, etc. The dialyzate must be at the same temperature as the blood this usually being effected by thermostatic control. Oxygen may be bubbled into the dialyzate so as to maintain the oxygen content of blood in a normal condition. The kidney machine may also contain a pump and means to introduce anticoagulants such as hirudin or heparin into the blood to prevent clotting of the blood on all surfaces of the apparatus that are in contact with blood.

A principle requirement of a kidney machine is that the semipermeable membrane should have a large surface area to insure adequate osmotic interchange between the blood and the dialyzate. This usually requires that the blood flow in a very thin film to provide maximum contact with the membrane bathed by the dialyzate liquid. Many configurations of kidney machines have been devised and are all compatible with the dialyzate treating section or unit of the invention. The blood dialyzate portion of the equipment may be in the form of a rotary drum apparatus in which a blood-filled flat cellophane tube is wound in helical fashion around a rotating drum made of wire mesh, the drum being bathed or submerged in dialyzate. A sandwich-type apparatus has been devised and can more readily be utilized for ultrafiltration under pressure. In this form of construction a flat cellophane bag is sandwiched between grooved plates of plastic. The dialyzate liquid flows through the grooves in the opposite direction to the flow of blood in the cellophane bag. However, this configuration provides dead flow spaces providing an inherent danger of clotting unless large amounts of anticoagulants are used. Another configuration is a twin-coil apparatus in which the semipermeable membrane is in the form of a flat, wide cellophane tube which is coiled in two tiers around the hollow core. The coils are mounted inside a container through which the rinsing liquid is passed. A very thin film of blood flows through the coils which present a large area of contact with the surrounding liquid. This has the advantage that the modules can be supplied, sterilized and ready to use inside the container and can be quickly and easily exchanged.

Hollow fibers also offer the advantage of high surface area in a very compact volume. Hollow fibers may be utilized for either or both of the membranes discussed herein. A more complete artificial kidney machine employing hollow fibers is illustrated in FIG. 3. In the kidney machine 40 of FIG. 3 a cylindrical container 42 houses the dialyzate chamber 44. The container 42 is surrounded with a heating jacket 46 such as an electric resistance heater powered by thermostatically controlled power unit 48. The cellulose acetate membrane is in the form of a plurality of fine filamentary hollow fibers 50 having their inlet ends potted to a common inlet header 52 and their outlet ends connected to a common outlet header 54. Each of the headers 52 and 54 can be threadingly and sealingly received into the side walls 56, 58 of the container 42.

The second membrane may also be in the form of a plurality of hollow fiber tubes containing the urease solution and connected to the common inlet and outlet headers as in the blood chamber described above. However, since there is no need to recirculate the urease solution the dialyzate treating chamber can be in the form of a cartridge 60 in which the plurality of hollow fibers 62 have both ends connected to a base 62 which is threadingly received into a wall 58 of the container 42. A further replaceable cartridge element 64 may be provided in the chamber containing an effective absorbent such as activated carbon to remove other impurities from the dialyzate.

The kidney machine 40 of FIG. 3 is utilized by filling the chamber 44 with dialyzate through inlet plug 66. The absorbent cartridge 64, dialyzate treating cartridge 60 and blood cartridge 68 are inserted. The heater 48 is turned on and a first catheter 70 is inserted into a vein of the subject and connected to blood outlet 72 and a second catheter 74 is inserted into an artery of the subject and connected to the pump 76. The pump is then energized and as blood is drawn from the artery and through the hollow fiber tubes 50 of the blood cartridge, urea passes into the common body of dialyzate 44 and then through the walls of hollow fiber tubes 62 of the cartridge 60 where urea is decomposed and retained therein. However, the positively charged walls of the hollow fibers 62 prevent the ammonium ions from entering the dialyzate and prevent metal cations from the dialyzate from entering the tubes 62. Other impurities are absorbed onto the granules 78 of activated carbon within the cartridge 64. As the urease containing cartridge 60 is exhausted a new cartridge is inserted. Similarly, the activated carbon cartridge 64 can be replaced as needed. Should the hollow fibers of the blood cartridge 68 become damaged or worn out, that unit can be replaced. Any of the cartridges can be readily removed for sterilization.

An example of practice follows.

Two cylindrical chambers of about 30 mls. capacity were separated by a positively charged membrane (RAI P-4025 membrane) having a surface area of about one square inch. Synthetic test solutions were introduced on each side of the membrane. The synthetic dialyzate contained about 2 gm/liter of urea, 4.5 gm/liter of sodium acetate trihydrate and 5.8 gm/liter of sodium chloride. The urease chamber test solution contained about 1 gm/liter of urease, 4.5 gm/liter sodium acetate trihydrate and 5.8 gm/liter of sodium chloride.

After six hours analysis showed that the quantity of urea in dialyzate had dropped about 25% and that significant concentrations of ammonium were present in the urease chamber. After 20 hours, urea concentration had dropped 45% and about 90% of the ammonia was present in the urease chamber, but the urease chamber now is found to contain no urea.

The above experiment demonstrates that urea readily diffuses through the membrane and is rapidly hydrolyzed to ammonium bicarbonate. The initial rate of removal of urea from dialyzate was about 0.1 gm/hr and about 0.05 gm/hr after 20 hours for the 4–5 mil thick film utilized. Higher diffusion rates can be expected with thinner membranes. The positively charged membrane also demonstrated the ability to isolate the toxic ammonium ion from the dialyzate and to retain the essential metal cations within the dialyzate. Preliminary estimates indicate that the dialyzate membrane need only require 24 in$^2$ of surface area to be compatible with the urea production of conventional hemodialysis units. A cartridge or treating chamber could readily be housed in a 1 ft. $\times$ 2 in. $\times$ 2 in. unit which is well within design constraints for continuous operation in portable or wearable artificial kidney apparatus for a typical thrice weekly dialysis regimen. Urease enzyme is not expensive and can readily be recharged for the next dialysis treatment.

The urease solution could be pumped past the membrane and removed from the chamber for continuous replenishment of urease and removal of ammonium ions. Similarly the dialyzate could be continuously pumped in concurrent or countercurrent flow past both membranes to increase urea transfer rate from the blood into the dialyzate. Another configuration would be to encapsulate the urease within a positively charged polymeric membrane and place the capsules in-line in the dialyzate flow path to absorb urea from the dialyzate while retaining ammonium salts within the capsules.

The cationic polymer membrane can also be utilized to form a single membrane, low dialyzate volume artificial kidney machine. Referring now to FIG. 4, the machine 70 includes a container 72 divided into a blood chamber 74 and a dialyzate chamber 76 by means of a cationic membrane 78. The membrane 78 repels and prevents passage of $NH_4^+$ ions 80 and $M^+$ ions 82. Therefore the dialyzate need not contain equilibrium concentrations of the essential cations such as strontium or calcium.

The blood chamber 74 contains an inlet 84 and an outlet 86. As the blood flows past the membrane 78, essential large proteins, cellular constituents and cations are retained in the blood, while urea 88 traverses the membrane 78, enters the dialyzate chamber 76 and is decomposed into $NH_4^+$ and $HCO_3^-$. The ammonium ion is retained in the dialyzate chamber. Substantially smaller amounts of dialyzate are required compared to dilution and continuous flowing dialyzate configurations.

It is to be realized that only preferred embodiments of the invention have been described and that numerous substitutions, modifications and alterations are permissible without departing from the spirit and scope of the invention as defined in the following claims.

What is claimed is:

1. A system for selectively removing urea from an aqueous liquid containing urea and positive metal cations comprising in combination:
    a container divided into a first chamber and a second chamber by means of a continuous sheet of cationically charged polymeric membrane selectively permeable to urea and having low permeability to cations;
    said first chamber including means for receiving said liquid; and
    said second chamber receiving a solution containing a urea decomposition agent whereby said cations are repelled by said membrane and retained in said liquid and urea permeates through the membrane into the solution and is decomposed into bicarbonate and ammonium, the ammonium being retained in the solution in the second chamber.

2. A system according to claim 1 in which the membrane contains quaternary ammonium groups.

3. A system according to claim 2 in which the membrane is a vinyl pyridine grafted polyethylene.

4. A system according to claim 1 in which the membrane has a thickness from 1 to 15 mils.

5. A system according to claim 4 in which the membrane has an exchange capacity of 1 to 20 meq/gm.

6. A system according to claim 1 in which the first chamber is a hollow body having said membrane as one wall thereof and having an inlet and outlet for flowing said liquid past a first surface of the membrane.

7. A system according to claim 1 in which the urea decomposition agent is urease.

8. A system according to claim 7 in which the urease concentration of the solution is at least 25% by weight of the urea content of the liquid.

9. A system according to claim 7 in which the liquid is dialyzate containing urea and further including a blood dialysis membrane selectively permeable to urea having one surface in contact with said dialyzate and a second surface for contacting a flow of blood.

10. A method of selectively removing urea from an aqueous liquid containing urea and positive metal cations comprising the steps of:
    placing the liquid in contact with a first surface of a cationically charged polymeric membrane selectively permeable to urea and having low permeability to cations;
    placing an urea decomposition solution containing an urea decomposition agent in contact with a second surface of the membrane; and
    selectively permeating urea from the liquid through the membrane into the solution thereby decomposing urea into ammonium cations and bicarbonate whereby the ammonium cations are retained in the decomposition solution and the metal cations are retained in the liquid.

11. A method according to claim 10 in which the membrane contains quaternary ammonium groups.

12. A method according to claim 11 in which the membrane has an exchange capacity of from 1 to 20 meq/gm.

13. A method according to claim 12 in which the membrane is a vinyl pyridine grafted polyethylene having a thickness from 1 to 15 mils.

14. A method according to claim 11 in which the agent is urease.

15. A method according to claim 14 in which the urease concentration of the decomposition solution is at least 25% of the concentration of urea in the urea containing liquid.

16. A method according to claim 14 in which the urea containing liquid is dialyzate from a blood dialysis unit.

17. A method according to claim 14 in which the urea containing liquid is blood.

18. An artificial kidney machine comprising in combination:
    enclosure means having an inlet and an outlet, and having a wall surface formed of a cationically charged membrane defining a channel for flowing urea containing blood past one surface of the membrane;
    urea removal means comprising walls defining a chamber, said chamber including a solution of urease having a concentration at least 25% by weight of the urea content of the blood; and
    means for supplying the urea permeate from the second surface of the membrane to the urease solution.

19. A machine according to claim 18 in which the membrane forms a common wall portion of said channel and chamber.

* * * * *